(12) United States Patent
Minatelli et al.

(10) Patent No.: US 9,238,043 B2
(45) Date of Patent: *Jan. 19, 2016

(54) COMPOSITION AND METHOD TO ALLEVIATE JOINT PAIN USING ALGAE BASED OILS

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/217,515

(22) Filed: Mar. 18, 2014

(65) Prior Publication Data

US 2014/0199342 A1 Jul. 17, 2014

Related U.S. Application Data

(63) Continuation-in-part of application No. 13/914,725, filed on Jun. 11, 2013, now Pat. No. 8,945,608, which is a continuation of application No. 12/840,372, filed on Jul. 21, 2010, now Pat. No. 8,481,072.

(60) Provisional application No. 61/227,872, filed on Jul. 23, 2009, provisional application No. 61/345,652, filed on May 18, 2010.

(51) Int. Cl.
| | | |
|---|---|---|
| A61K 47/00 | (2006.01) |
| A61K 31/728 | (2006.01) |
| A61K 31/202 | (2006.01) |
| A61K 31/122 | (2006.01) |
| A61K 36/9066 | (2006.01) |
| A61K 45/06 | (2006.01) |
| A61K 35/612 | (2015.01) |
| A61K 36/05 | (2006.01) |
| A61K 36/185 | (2006.01) |
| A61K 36/324 | (2006.01) |
| A61K 36/74 | (2006.01) |
| A61K 31/685 | (2006.01) |
| A61K 31/7028 | (2006.01) |
| A23L 1/30 | (2006.01) |

(52) U.S. Cl.
CPC ............. *A61K 31/728* (2013.01); *A23L 1/3006* (2013.01); *A23L 1/3008* (2013.01); *A61K 31/122* (2013.01); *A61K 31/202* (2013.01); *A61K 31/685* (2013.01); *A61K 31/7028* (2013.01); *A61K 35/612* (2013.01); *A61K 36/05* (2013.01); *A61K 36/185* (2013.01); *A61K 36/324* (2013.01); *A61K 36/74* (2013.01); *A61K 36/9066* (2013.01); *A61K 45/06* (2013.01); *A23V 2002/00* (2013.01)

(58) Field of Classification Search
CPC .................................................. A61K 36/9066
See application file for complete search history.

(56) References Cited

U.S. PATENT DOCUMENTS

| | | | |
|---|---|---|---|
| 4,801,539 A | 1/1989 | Akasaka et al. |
| 5,527,533 A | 6/1996 | Tso et al. |
| 6,800,299 B1 | 10/2004 | Beaudoin et al. |
| 7,241,463 B2 | 7/2007 | Nielsen |
| 7,247,752 B2 | 7/2007 | Lockwood et al. |
| 8,030,037 B2 | 10/2011 | Thomas et al. |
| 8,481,072 B2 | 7/2013 | Minatelli et al. |
| 8,591,912 B1 | 11/2013 | Kadam et al. |
| 2003/0078304 A1 | 4/2003 | Andersson et al. |
| 2003/0091652 A1 | 5/2003 | Ishaq |
| 2003/0096794 A1 | 5/2003 | Niehoff |
| 2004/0180025 A1 | 9/2004 | Long et al. |
| 2004/0180851 A1 | 9/2004 | Long et al. |
| 2004/0234587 A1 | 11/2004 | Sampalis |
| 2004/0241249 A1 | 12/2004 | Sampalis |
| 2006/0078625 A1 | 4/2006 | Rockway |
| 2007/0098808 A1 | 5/2007 | Sampalis |
| 2007/0196894 A1 | 8/2007 | Sim et al. |
| 2007/0270376 A1 | 11/2007 | Chandler |
| 2008/0014282 A1 | 1/2008 | Long et al. |
| 2008/0038780 A1 | 2/2008 | Stocks et al. |
| 2008/0166779 A1 | 7/2008 | Thomas et al. |

(Continued)

FOREIGN PATENT DOCUMENTS

| | | |
|---|---|---|
| CN | 102746947 | 10/2012 |
| EP | 0601698 | 6/1994 |

(Continued)

OTHER PUBLICATIONS

Nir et al., "BioAstin Helps Relieve Pain and Improves Performance on Patients With Rheumatoid Arthritis," Health Research and Studies Center, Los Altos, California, Study Report, May 3, 2002, 8 pages.

(Continued)

*Primary Examiner* — Bin Shen

(74) *Attorney, Agent, or Firm* — Allen, Dyer, Doppelt, Milbrath & Gilchrist, P.A.

(57) ABSTRACT

A dietary supplement composition is formulated in a therapeutic amount to treat and alleviate symptoms of joint pain in a patient. The composition includes an algae based oil having glycolipids and phospholipids and Eicosapentaenoic (EPA) fatty acids in combination with astaxanthin and low molecular weight hyaluronic acid or sodium hyaluronate (hyaluronan) and a molecular weight less than 300 kilodaltons (kDa) in an oral dosage form.

12 Claims, 1 Drawing Sheet

(56) References Cited

U.S. PATENT DOCUMENTS

| | | |
|---|---|---|
| 2009/0061067 A1 | 3/2009 | Tilseth et al. |
| 2009/0170808 A1 | 7/2009 | Ling et al. |
| 2009/0181114 A1 | 7/2009 | Minatelli et al. |
| 2009/0181127 A1 | 7/2009 | Minatelli et al. |
| 2009/0258081 A1 | 10/2009 | Minatelli et al. |
| 2010/0143571 A1 | 6/2010 | Breivik |
| 2010/0236137 A1 | 9/2010 | Wu et al. |
| 2010/0291053 A1 | 11/2010 | Clayton et al. |
| 2011/0020316 A1 | 1/2011 | Minatelli et al. |
| 2011/0117207 A1 | 5/2011 | Minatelli et al. |
| 2011/0195061 A1 | 8/2011 | Minatelli et al. |
| 2011/0268811 A1 | 11/2011 | Minatelli et al. |
| 2013/0059768 A1 | 3/2013 | Hallaraker et al. |
| 2013/0287756 A1 | 10/2013 | Minatelli et al. |

FOREIGN PATENT DOCUMENTS

| | | |
|---|---|---|
| EP | 1724357 | 11/2006 |
| GB | 2 103 088 | 2/1983 |
| IN | 201526 | 2/2007 |
| JP | 2005521629 | 7/2005 |
| WO | 03/027267 | 4/2003 |
| WO | 2004/080388 | 9/2004 |
| WO | 2004/112776 | 12/2004 |
| WO | 2011/062953 | 5/2011 |
| WO | 2013/032333 | 3/2013 |
| WO | 2014/013335 | 1/2014 |
| WO | 2014/014766 | 1/2014 |

OTHER PUBLICATIONS

Balogh et al., "Absorption, Uptake and Tissue Affinity of High-Molecular-Weight Hyaluronan After Oral Administration in Rats and Dogs," Journal of Agricultural and Food Chemsitry, published Oct. 30, 2008, pp. 10582-10593.

Gotoh et al., "Effects of the Molecular Weight of Hyaluronic Acid and its Action Mechanisms on Experimental Joint Pain in Rats," Annal of the Rheumatic Diseases, 1993, 52:817-822.

Mendes-Pinto et al., "Evaluation of Different Cell Disruption Processes on Encrysted Cells of Haematococcus Pluvialis: Effects on Astaxanthin Recovery and Implications for Bio-Availability," Journal of Applied Phycology, vol. 13, No. 1, Feb. 2001, pp. 19-24.

Nobre et al., "Supercritical Carbon Dioxide Extraction of Astaxanthin and Other Carotenoids from the Microalga Haematococcus Pluvialis," European Food Research and Technology, vol. 223, No. 6, Mar. 2006, pp. 787-790.

Valderrama et al., "Extraction of Astaxantine and Phycocyanin from Microalgae with Supercritical Carbon Dioxide," Journal of Chemical and Engineering Data, vol. 48, No. 4, Jul. 2003, pp. 827-830.

Mendes et al., "Applications of Supercritical CO2 Extraction to Microalgae and Plants," Journal of Chemical Technology and Biotechnology, vol. 62, No. 1, Jan. 1995, pp. 53-59.

Calder, "Polyunsaturated Fatty Acids amd Inflammation: Therapeutic Potential in Rheumatoid Arthritis," Current Rheumatology Reviews 2009, vol. 5, No. 4, Nov. 2009, pp. 214-225.

Calder, "Joint Nutrition Society and Irish Nutrition and Dietetic Institute Symposium on Nutrition and Autoimmune Disease PUFA, Inflammatory Processes and Rheumatoid Arthritis," Proceedings of the Nutrition Society, vol. 67, No. 4, Nov. 2008, pp. 409-418.

Hurst et al., "Dietary Fatty Acids and Arthritis," Prostaglandins, Leukotrienes and Essential Fatty Acids, vol. 82, No. 4-6, Apr. 2010, pp. 315-318.

Sales et al., "Fish Oil Supplementation in Rheumatoid Arthritis," Reumatismo, vol. 60, No. 3, Jul. 2008, pp. 174-179.

Kikuchi et al., "Bibliographical Investigation of Complementary Alternative Medicines for Osteoarthritis and Rheumatoid Arthritis," Geriatrics and Gerontology International, vol. 9, No. 1, 2009, pp. 29-40.

Deutsch, "Evaluation of the Effect of Neptune Krill Oil Chronic Inflammation and Arthritic Symptoms," Journal of the American College of Nutrition, vol. 26, No. 1, pp. 39-47 (2007).

Bunea et al., "Evaluation of the Effects of Neptune Krill Oil on the Clinical Course of Hyperlipidemia," Alternative Medicine Review, vol. 9, No. 4, pp. 420-428 (2004).

Lee et al., "Astaxanthin Inhibits Nitric Oxide Production and Inflammatory Gene Expression by Supressing IKB Kinase-Dependent NF-kB Activation," Molecules and Cells, Jun. 2003, vol. 16, No. 1, pp. 97-105.

Ohgami et al., "Effects of Astaxanthin on Lipopolysaccharide-Induced Inflammation In Vitro and In Vivo," Investigative Opthalmology & Visual Science, Jun. 2003, vol. 44, No. 6, pp. 2694-2701.

Mummert et al., "Synthesis and Surface Expression of Hyaluronan by Dendritic Cells Its Potential Role in Antigen Presentation," Journal of Immunology 2002, pp. 4322-4331.

Termeer et al., "Hyaluronan—Magic Glue for the Regulation of the Immune Response?" Trends in Immunology, vol. 24, No. 3, Mar. 2003, pp. 112-114.

McKee et al., "Hyaluronan Fragments Induced Nitric-Oxide Synthase in Murine Macrophages Through a Nuclear Factor kB-Dependent Mechanism," Journal of Biological Chemistry, vol. 272, No. 12, Mar. 21, 1997, pp. 8013-8018.

Brown et al., "Turnover of Hyaluronan in Synovial Joints: Elimination of Labelled Hyaluronan from the Knee Joint of the Rabbit," Experimental Physiology, 1991, No. 76, pp. 125-134.

Serhan et al., "Resolution of Inflammation: State of the Art, Definitions and Terms," The FASEB Journal, vol. 21, Feb. 2007, pp. 325-332.

Moreland, "Intra-Articular Hyaluronan (Hyaluronic Acid) and Hylans for the Treatment of Osteoarthritis: Mechanisms of Action," University of Alabama at Birmingham, Arthritis Research & Therapy, vol. 5, No. 2, Jan. 2003, pp. 54-67.

Lee et al., "Hyaluronan: A Multifunctional, MegaDalton, Stealth Molecule," Current Opinion in Cell Biology, 2000, pp. 581-586.

Kalman et al., "Effect of a Natural Extract of Chicken Combs with a High Content of Hyaluronic Acid (Hyal-Joint®) on Pain Relief and Quality of Life in Subjects with Knee Osteoarthritis: A Pilot Randomized Double-Blind Placebo-Controlled Trial," Nutrition Journal, Jan. 2008, pp. 1-9.

Necas et al., "Hyaluronic Acid (Hyaluronan): A Review," Veterinami Medicina, vol. 53, 2008, pp. 397-411.

Nishimoto et al., "Effect of Chondroitin Sulfate and Hyaluronic Acid on Gene Expression in a Three-Dimensional Culture of Chondrocytes," Journal of Bioscience and Bioengineering, vol. 100, No. 1, 2005, pp. 123-126.

Yamawaki et al., "Hyaluronan Receptors Involved in Cytokine Induction in Monocytes," Glycobiology, vol. 19, No. 1, 2009, pp. 83-92.

Lee et al., "Production of Astaxanthin by Haematococcus," Chemical from Microalgae, Ed: Zvi Cohen, Taylor and Francis, UK (1999), pp. 173-195.

Bjerkeng et al., "Bioavailability of all-E-astaxanthin and Z-isomers of Astaxanthin in Rainbow Trout (Oncorhynchus Mykiss)," Aquaculture, vol. 157, Issues 1-2, Nov. 1997, pp. 63-82; Abstract Only (2 pages).

Yang et al., "Glioma-Associated Hyaluronan Induces Apoptosis in Dendritic Cells via Inducible Nitric Oxide Synthase: Implications for the use of Dendritic Cells for Therapy of Gliomas," Cancer Res.; May 2002; 62(9):2583-91; Abstract Only (2 pages).

Ghosh et al., "Potential Mechanism of Action of Intra-Articular Hyaluronan Therapy in Osteoarthritis: Are the Effects Molecular Weight Dependent?" Semin Arthritis Rheum.; Aug. 2002; 32(1):10-37; Abstract Only (2 pages).

Rooney et al., "Angiogenic Oligosaccharides of Hyaluronan Enhance the Production of Collagens by Endothelial Cells," Journal of Cell Science; May 1993; 105 (Pt 1):213 218; Abstract Only (1 page).

Ruff et al., "Eggshell Membrane in the Treatment of Pain and Stiffness from Osteoarthritis of the Knee: A Randomized, Multicenter, Double-blind, Placebo Controlled Clinical Study," Clinical Rheumatology, Aug. 2009; 28(8):907-914; Abstract Only (1 page).

Schiedt et al., "Natural Occurrence of Enantiomeric and Meso-Astaxanthin, 5, Ex Wild Salmon (Salmo Salar and Oncorhynchus)," Helv. Chim. Acta; 1981; 64(2):449-57; Abstract Only (1 page).

Jiang et al., "Hyaluronan in Tissue Injury and Repair," Annu Rev Cell Dev Biology; 2007;23:435-51; Abstract Only (1 page).

(56) References Cited

OTHER PUBLICATIONS

Noble, "Hyaluronan and its Catabolic Products in Tissue Injury and Repair," Matrix Biology; Jan. 2002; 21(1):25-9; Abstract Only (1 page).

Stern et al., "Hyaluronan Fragments: An Information-Rich System," European Journal of Cell Biology; Aug. 2006; 85(8):699-715; Abstract Ony (1 page).

Ruff et al., "Eggshell Membrane in the Treatment of Pain and Stiffness from Osteoarthritis of the Knee: A Randomized, Multicenter, Double-blind, Placebo Controlled Clinical Study" Clincal Rheumatology; Journal of the International League of Associations for Rheumatology; vol. 28, No. 8; Apr. 2009; pp. 907-914.

Ruff et al., "Eggshell Membrane: A Possible New Natural Therapeutic for Joint and Connective Tissue Disorders, Results from Two Open-Label Human Clincal Studies," Clinical Interventions in Aging 2009 LNKD-PUBMED: 19554094, vol. May 2009, pp. 235-240.

Ierna et al., "Supplementation of Diet with Krill Oil Protects Against Experimantal Rheumatoid Arthritis," BMC Musculoskeletal Disorders 2010 LNKD-PUBMED: 20587038, vol. 11, 2010, 11 pages.

Bergin et al., "Oral Hyaluronan Gel Reduces Post Operative Tarsocrural Effusion in the Yearling Thoroughbroed," Equine Veterinary J, 2006, 38(4):375-378.

Guerin et al., "Haematococcus Astaxanthin: Applications for Human Health and Nutrition," Trends in Biotechnology, 2003, 21 (5):210-216.

Peer et al., "Tumor-Targeted Hyaluronan Hanollposomes Increase the Antitumor Activity of Liposomal Doxorubicin in Syngeneic and Human Xenograft Mouse Tumor Models," Neoplasia, 2004, 6(4):343-353.

Tou et al., "Krill for Human Consumption: Nutritonal Value and Potential Health Benefits," Nutrition Reviews, vol. 65, No. 2, Feb. 2007, pp. 63-77.

Gavio et al., "Grateloupia Tututuru (Halymeniacea, Rhodophyta) is the Correct Name of the Non-Native Species in the Atlantic Known as Grateloupia Doryphora," Eur. J. Phycol. (2002), 37:349-359.

Kagan et al., "Acute Appearance of Fatty Acids in Human Plasma—A Comparative Study Between Polar-Lipid Rich Oil from the Microalgae Nannochloropis Oculata in Krill Oil in Healthy Young Males," as published in Lipids in Health and Disease, 2013, 12:102.

Daniels, Stephen "Glycolipids, salts, and wax esters: GOED's Ismall outlines next generation omega-3 forms to watch" http://www.nutraingredients-usa.com/content/view/print/88201; pp. 3; printed Feb. 17, 2014.

Khozin-Goldberg et al., Biosynthesis of eicosapenteanoic acid (EPA) in the freshwater eustigmatophyte monodus subterraneus (uestigmatophyceae) J.Phycol. 38, 745-756 (2002).

Maharjan et al., "High and Low Molecular Weight Hyaluronic Acid Differentially Regulate Human Fibrocyte Differentiation," PLoS ONE, Oct. 2011, vol. 6, Issue 10, pp. 1-10.

Itano et al., "Three Isoforms of Mammalian Hyaluronan Synthases Have Distinct Enzymatics Properties," The Journal of Biological Chemistry, vol. 274, No. 35, Aug. 27, 1999; pp. 25085-25092.

Goldberg et al., "Intra-Articular Hyaluronans: The Treatment of Knee Pain in Osteoarthritis," Journal of Pain Research, 2010:3; pp. 51-56.

Gariboldi et al., "Low Molecular Weight Hyaluronic Acid Increases the Self-Defense of Skin Epithelium by Induction of β-Defensin 2 via TLR2 and TLR4," The Journal of Immunology, 2008; downloaded on Sep. 25, 2014, pp. 2103-2110.

Capelli et al., "Astaxanthin—Natural Astaxanthin; King of the Carotenoids," Published by Cyariotech Corporation 2008, pp. 1-148.

Guerin et al., "Haematococcus Astaxanthin: Applications for Huaman Health and Nutrition," Trends in Biotechnology, vol. 21, No. 5, May 2003, pp. 210-216.

Spiller et al., "Safety of an Astaxanthin-Rich Haematococcus Pluvialis Algal Extract: A Randomized Clinical Trial." Journal of Medicinal Food, vol. 6, No. 1, 2003 pp. 51-56.

Khanafari et al., "Extraction of Astaxanthin Esters From Shrimp Waste by Chemical and Microbial Methods," Iran. J. Environ. Health. Sci. Eng., 2007, vol. 4, No. 2, pp. 93-98.

Nuno et al., "Effects of the Marine Microalgae Isochrysis Galbana and Nannochloropsis Oculata in Diabetic Rats," Journal of Functional Foods, vol. 5, No. 1, Jan. 2013, pp. 106-115.

Deutsch, "Evaluation of the Effect of Neptune Krill Oil on Chronic Inflammation and Arthritic Symptoms," Journal of the American College of Nutrition, vol. 26, No. 1, Feb. 2007, pp. 39-48.

Hurst et al., "Dietary Fatty Acids and Arthritis," Prostaglandins, Leukotrienes and Essential Fatty Acids, vol. 82, No. 4-6, Apr. 1, 2010, pp. 315-318.

Ierna et al, "Supplementation of Diet With Krill Oil Protects Against Experimental Rheumatoid Arthritis," BMC Musculoskeletal Disorders, Biomed Central Ltd., vol. 11, No. 1, Jun. 29, 2010, 11 pages.

Ruff et al., "Eggshell Membrane in the Treatment of Pain and Stiffness from Osteoarthritis of the Knee: A Randomized, Multicenter, Double-blind, Placebo Controlled Clinical Study," Clinical Rheumatology; Journal of the International League of Associations for Rheumatology; vol. 28, No. 8; Apr. 2009; pp. 907-914.

Ruff et al., "Eggshell Membrane: A Possible New Natural Therapeutic for Joint and Connective Tissue Disorders. Results from Two Open-Label Human Clinical Studies," Clinical Interventions in Aging 2009; vol. 4, May 2009, pp. 235-240.

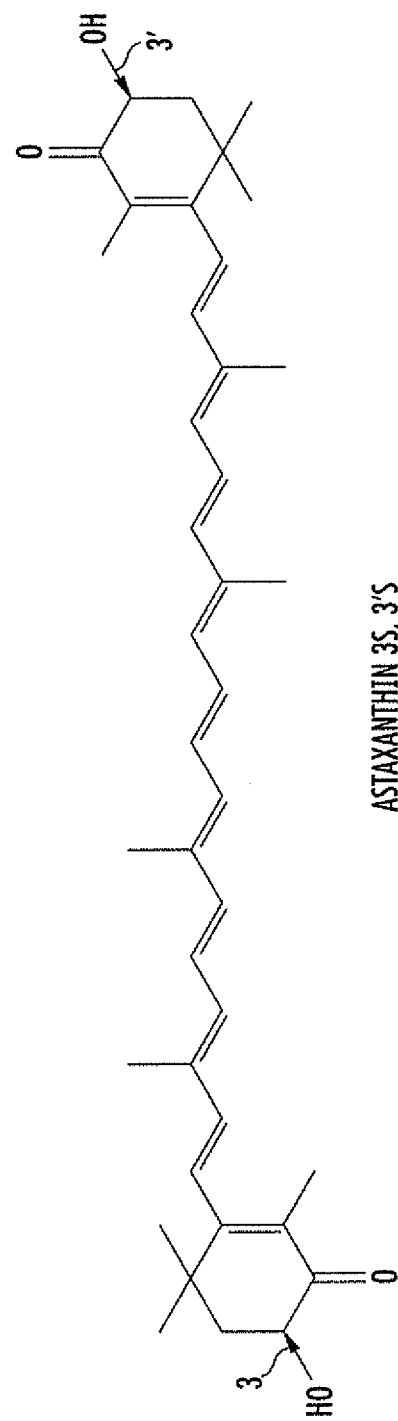

COMPOSITION AND METHOD TO ALLEVIATE JOINT PAIN USING ALGAE BASED OILS

RELATED APPLICATION(S)

This application is a continuation-in-part application of Ser. No. 13/914,725 filed Jun. 11, 2013 (now U.S. Pat. No. 8,945,608), which is a continuation application of Ser. No. 12/840,372 filed Jul. 21, 2010 (now U.S. Pat. No. 8,481,072), which is based upon provisional application Ser. No. 61/227,872 filed Jul. 23, 2009; and provisional application Ser. No. 61/345,652 filed May 18, 2010, the disclosures which are hereby incorporated by reference in their entirety.

FIELD OF THE INVENTION

This invention relates to treating and alleviating joint pain and symptoms of osteoarthritis and/or rheumatoid arthritis using therapeutic compositions and methods derived from algae based oils and synergistic additives.

BACKGROUND OF THE INVENTION

The use of krill and/or marine oil are disclosed in U.S. Patent Publication Nos. 2004/0234587; 2004/0241249; and 2007/0098808, the disclosures which are hereby incorporated by reference in their entirety. The beneficial aspects of using krill and/or marine oil are shown also in a research paper published by L. Deutsch as "Evaluation of the Effect of Neptune Krill Oil on Chronic Inflammation and Arthritic Symptoms," published in the Journal of the American College of Nutrition, Volume 26, No. 1, 39-49 (2007), the disclosure which is hereby incorporated by reference in its entirety.

The commonly assigned and incorporated by reference '725 parent and '372 grandparent applications identified above are directed to the advantageous use of krill and/or marine oils. The beneficial and therapeutic advantages of krill oil alone are discussed in the various research endeavors that are mentioned in the Background of the Invention section of those applications.

The commonly assigned and incorporated by reference '725 parent and '372 grandparent applications disclose the beneficial and synergistic effects of alleviating joint pain when krill oil and/or marine oil is used in combination with other active constituents such as the low molecular weight hyaluronic acid and astaxanthin. Although use of krill oil in those applications was one focus, those applications also disclosed that the composition may use fatty acid rich oils derived from algae. A marine based or other algae based oil as an example includes phospholipid and glycolipid bound EPA (Eicosapentaenoic acid) as compared to fish oils that are triacylglycerides. Further development has been accomplished with different algae species that produce EPA alone or EPA and DHA (Docosahexaenoic acid) so that an algae based oil is advantageously used in place of krill oil with the composition and methodology as disclosed in the '725 parent and '372 grandparent applications.

SUMMARY OF THE INVENTION

In accordance with a non-limiting example, an algae based oil is used in place of a krill oil to treat and alleviate symptoms of joint pain in a patient by administering a therapeutic amount of a dietary supplement composition, including an algae based oil in combination with astaxanthin and low molecular weight polymers of hyaluronic acid or sodium hyaluronate (hyaluronan).

The algae based oil is a marine based algae oil in one non-limiting example and includes EPA conjugated with phospholipid and glycerolipid as glycolipid bound polar lipids. It may include DHA also conjugated with the phospholipid and glycolipid bound polar lipids. In one example, the algae based oil has an EPA titre higher than DHA and contains phospholipid and glycolipid bound EPA as compared to fish oils that are triacylglycerides. Different algae species may be used that produce EPA alone or EPA and DHA, including those algae species such as *nannochloropsis oculata* for EPA production and various diatom species of microalgae.

A dietary supplement composition is formulated in a therapeutic amount to treat and alleviate symptoms of joint pain in a patient. The composition includes an algae based oil having glycolipids and phospholipids and Eicosapentaenoic (EPA) fatty acids in combination with astaxanthin and low molecular weight hyaluronic acid or sodium hyaluronate (hyaluronan) having a molecular weight less than 300 kilodaltons (kDa) in an oral dosage form.

In one example, the low molecular weight hyaluronic acid or sodium hyaluronate (hyaluronan) has a molecular weight less than 230 kDa and in another example the low molecular weight hyaluronic acid or sodium hyaluronate (hyaluronan) has a molecular weight of between 0.5 and 100 kDa.

In yet another example, the algae based oil includes Eicosapentaenoic (EPA) and Docosahexaenoic (DHA) fatty acids in the form of glycolipids and phospholipids. In one non-limiting example, the algae based oil may be formed from 5-10 percent phospholipids and 35-40 percent glycolipids. In yet another example the algae based oil includes at least 15 percent EPA. The EPA fatty acids are conjugated with phospholipid and glycolipid polar lipids in an example.

In an example, the algae based oil may be derived from the microalgae *Nannochloropsis oculata* comprising Eicosapentaenoic (EPA) fatty acids in the form of glycolipids and phospholipids. The algae based oil may also be derived from the microalgae selected from the group consisting of *thalassiosira* sp., *tetraselmis* sp., *chaetoceros* sp., and *isochrysis* sp., and comprising Eicosapentaenoic (EPA) and Docosahexaenoic (DHA) fatty acids in the form of glycolipids and phospholipids.

The algae based oil may be derived from the microalgae selected from the group consisting of *grateloupia turuturu; porphyridium cruentum; monodus subterraneus; phaeodactylum tricornutum; isochrysis galbana; navicula* sp.; *pythium irregule; nannochloropsis* sp.; and *nitzschia* sp. and comprising Eicosapentaenoic (EPA) and Docosahexaenioic (DHA) fatty acids in the form of glycolipids and phospholipids.

The algae based oil may be derived from the microalgae selected from the group consisting of *Asterionella japonica, Bidulphia sinensis, Chaetoceros septentrionale, Lauderia borealis, Navicula biskanteri, Navicula laevis* (heterotrof.), *Navicula laevis, Navicula incerta, Stauroneis amphioxys, Navicula pellicuolsa, Bidulphia aurtia, Nitzschia alba, Nitzschia chosterium, Phaeodactylum tricornutum, Phaeodactylum tricornutum, Skeletonema costatum, Pseudopedinella* sp., *Cricosphaera elongate, Monodus subterraneus, Nannochloropsis, Rodela violacea* 115.79, *Porphyry. Cruentum* 1380.Id, *Pavlova sauna, Cochlodinium heteroloblatum, Cryptecodinium cohnii, Gonyaulax catenella, Gyrodinium cohnii, Prorocentrum minimum, Chiorella minutissima, Isochrysis galbana* ALII4, *Phaeodactylum tricornutum* WT, *Porphyridium cruentum*, and *Monodus subterraneus* and comprising Eicosapentaenoic (EPA) and Docosahexaenoic (DHA) fatty acids in the form of glycolipids and phospholipids.

The algae based oil may be derived from a fungi selected from the group consisting of *Mortierella alpine, Mortierella alpine* IS-4, and *Pythium irregulare*, or a bacteria as SCRC-2738 and comprising Eicosapentaenoic (EPA) and Docosahexaenoic (DHA) fatty acids in the form of glycolipids and phospholipids. In an example, 1-4000 mg of algae based oil per daily dose may be delivered and in yet another example 0.1-50 mg astaxanthin supplemented to the algae based oil per daily dose may be delivered.

The astaxanthin is derived from *Haematococcus pluvialis* algae, *Pfaffia*, krill, or by synthetic routes, in the free diol, monoester or diester form in an example. The low molecular weight hyaluronic acid or sodium hyaluronate (hyaluronan) in an example are derived from microbial fermentation or animal tissue. It is possible to deliver 1-500 mg of hyaluronan per daily dose. The hyaluronic acid is derived from a biofermentation process in another example.

BRIEF DESCRIPTION OF THE DRAWINGS

Other objects, features and advantages of the present invention will become apparent from the detailed description of the invention which follows, when considered in light of the accompanying drawings in which:

FIG. 1 is a view showing a chemical structure of astaxanthin that can be used in accordance with a non-limiting example.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It is known that algae can be an important source for omega-3 fatty acids such as EPA and DHA. It is known that fish and krill do not produce omega-3 fatty acids but accumulate those fatty acids from the algae they consume. Omega-3 bioavailability varies and is made available at the site of physiological activity depending on what form it is contained. For example, fish oil contains omega-3 fatty acids in a triglyceride form that are insoluble in water and require emulsification by bile salts via the formation of micelles and subsequent digestion by enzymes and subsequent absorption. Those omega-3 fatty acids that are bound to polar lipids, such as phospholipids and glycolipids, however, are not dependent on bile for digestion and go through a simpler digestion process before absorption. Thus, these omega-3 fatty acids, such as from an algae based oil, have greater bioavailability for cell growth and functioning as compared to the omega-3 triglycerides of fish oil. There are many varieties of algae that contain EPA conjugated with phospholipid and glycolipid polar lipids or contain EPA and DHA conjugated with phospholipids and glycolipids.

Throughout this description, the term "algae" or "microalgae" may be used interchangeably to each other with microalgae referring to photosynthetic organisms that are native to aquatic or marine habitats and are too small to be seen easily as individual organisms with the naked eye. When the term "photoautotropic" is used, it refers to growth with light as the primary source of energy and carbon dioxide as the primary source of carbon. Other forms of biomass that may encompass algae or microalgae may be used and the term "biomass" may refer to a living or recently dead biological cellular material derived from plants or animals. The term "polar" may refer to the compound that has portions of negative and/or positive charges forming negative and/or positive poles. The term "oil" may refer to a combination of fractionable lipid fractions of a biomass. As known to those skilled in the art, this may include the entire range of various hydrocarbon soluble in non-polar solvents and insoluble, or relatively insoluble in water as known to those skilled in the art. The microalgae may also include any naturally occurring species or any genetically engineered microalgae to have improved lipid production.

There now follows a description of the joint health composition and associated method as based on the original disclosure in the '725 and '372 applications and related to the krill oil and marine based algae oil disclosed in these applications, followed by further details of the algae based oil and its composition and use relative to an algae based oil having phospholipid and glycolipid bound EPA or EPA and DHA. The algae based oil is substituted for the previous krill oil in those applications. The description will begin, however, with details of the previous disclosure in the parent and grandparent applications regarding the use of krill oil included in the composition, and then proceed with the description and details of the algae based oil. It should be understood that when krill oil is specifically described and its composition as related to the disclosure in the '725 and '372 parent and grandparent applications, the algae based oil may be substituted therefor. Some of the composition components will change such as the levels of EPA and/or EPA and DHA and other components when the algae based oil is used as later shown in various tables within the following description.

The composition as related to the krill oil disclosure in the parent and grandparent applications includes EPA and DHA functionalized as marine phospholipids and acyltriglycerides derived from krill. Both the krill and algae based oil compositions may include esterified astaxanthin, and in one non-limiting example, low molecular weight polymers of hyaluronic acid or sodium hyaluronate (hyaluronan) in an oral dosage form. Some of these components relative to the krill oil in an example are explained in the following chart:

| Components PHOSPHOLIPIDS | Percentage (%) |
|---|---|
| PC, PE, PI, PS, SM, CL | >40 |
| OMEGA-3 (functionalized on PL) | >30 |
| Eicosapentaenoid Acid (EPA)* | >17 (15% in one example and 10% in another) |
| Docosahexaenoid Acid (DHA)+ | >11 (9% in one example and 5% in another) |
| ANTIOXIDANTS | (mg/100 g) |
| Astaxanthin, Vitamin A, Vitamin E | >1.25 |

*>55% of PL-EPA/Total EPA
+>55% of PL-DHA/Total DHA
These amounts can vary depending on application and persons.

As noted before, surprisingly the composition includes a pro-inflammatory low molecular weight Hyaluronic Acid (LMWtHA). Natural high molecular weight hyaluronic acid is the major hydrodynamic component of synovial fluid and importantly is known to be immuno-neutral to the innate immune system. It is nature's bone joint shock absorber and lubricant. It has been found that there is excellent oral bioavailability of LMWtHA fragments specifically to connective tissue, which maximizes interaction with target synovial fluid producing cells. Therefore in a preferred composition containing krill oil or algae based oil, astaxanthin and LMWtHA, two anti-inflammatory components are thus combined with one highly inflammatory component. The scientific literature indicates that LMWtHA fragments exhibit potent pro-inflammatory behavior. It therefore remains unclear why a pro-inflammatory component would elicit a favorable overall response in inflamed joint tissues. It is believed that such pro-inflammatory LMWtHA fragments may promote site repair by simulation of the innate immune system repair mechanism and by simulating production of non-immunogenic high molecular weight HA bringing the joint back to homeostasis. However, these are theories. A great deal of work by leading immunologists is still attempting to unravel all the aspects of the complicated signaling processes associated with the innate immune system. Studies using large animal models of osteoarthritis have shown that mild immunogenic Hyaluronic Acids with molecular weights within the range of $0.5$-$1.0 \times 10^6$ Da (Dalton) were generally more effective in reducing indices of synovial inflammation and restoring the rheological properties of SF (visco-induction) than non-immunogenic HA's with molecular weights $>2.3 \times 10^6$ Da.

The range of low molecular weight hyaluronic acid has been considered by many skilled in the art to be around 300 kDa to about 320 kDa or less. Low molecular weight hyaluronic acids and sodium hyaluronates are well known to act as pro-inflammatory agents and assumed up-regulators of the inflammatory cascade with respect to the innate immune system. Some reports indicate that hyaluronic acid fragments induce expression of inflammatory genes and they are low molecular weight kDa. Clinical trials by the inventors and their assignee have shown the effectiveness of the composition when using krill oil, which may include an algae based oil, together with the low molecular weight hyaluronic acid or hyaluronan and astaxanthin in accordance with a non-limiting example. In the clinical trials, no rescue medication was allowed as compared to the trials published by Deutsch referenced above.

The composition and method in the clinical trials of the current subject matter were directed to treating and alleviating joint pain. The clinical subjects in the clinical trial did not have any confirmed osteoarthritis and/or rheumatoid arthritis. An abbreviated exclusion criteria listed specifically that subjects did not have any presence of auto-immune diseases or similar diseases and the study had excluded those subjects who knew their joint pain was due to osteoarthritis and/or rheumatoid arthritis. The clinical study was directed to patients that have a non-disease state joint pain that is not associated with a disease state such as osteoarthritis and/or rheumatoid arthritis. The composition was used as a supplement to treat and alleviate symptoms of joint pain of unknown etiology, including joint pain not associated with osteoarthritis and/or rheumatoid arthritis.

Astaxanthin is a component of the composition. The clinical trials of the joint care composition with the krill oil, low molecular weight hyaluronic acid and astaxanthin proved the effectiveness of the composition with surprising beneficial results. Related scientific literature indicates that in a lipopolysaccharide induced inflammatory rat model, astaxanthin at just 1 mg/kg in vitro and in vivo: (1) down regulates TNF-alpha production by 75%; (2) down regulates prostaglandin E-2 production (PGE-2) by 75%; (3) inhibits nitric oxide synthase (NOS) expression of nitric oxide by 58%; and (4) these effects on inflammatory markers were nearly as effective as prednisolone in this model. Such information suggests but does not prove that astaxanthin may be an effective standalone product for the reduction of OA and/or RH pain or other symptomology associated with OA and/or RH. FIG. 1 shows an example of the astaxanthin as astaxanthin 3S, 3'S (3,3'-dihydroxy-4,4'-diketo-β-carotene).

In induced uveitis, astaxanthin also showed dose dependant ocular anti-inflammatory activity by suppression of NO, PGE-2 and TNF-Alpha by directly blocking NO synthase activity. Astaxanthin is also known to reduce C-Reactive Protein (C-RP) blood levels in vivo. For example, in human subjects with high risk levels of C-RP three months of astaxanthin treatment resulted in 43% of patients serum C-RP levels to drop below the risk level. This may explain why C-RP levels dropped significantly in the Deutsch study. Astaxanthin is so powerful that it has been shown to negate the pro-oxidant activity of Vioxx, a COX-2 inhibitor belonging to the NSAIDS drug class which is known to cause cellular membrane lipid peroxidation leading to heart attack and stroke. For this reason Vioxx was removed from the US market. Astaxanthin is absorbed in vitro by lens epithelial cells where it suppresses UVB induced lipid peroxidative mediated cell damage at umol/L concentrations. In human trials astaxanthin at 4 mgs/day prevented post exercise joint fatigue following strenuous knee exercise when compared to untreated subjects. These results have been shown in:

1) Lee et al., Molecules and Cells, 16(1):97-105; 2003;
2) Ohgami et al., Investigative Ophthalmology and Visual Science 44(6):2694-2701, 2003;
3) Spiller et al., J. of the Amer. College of Nutrition, 21(5): October 2002; and
4) Fry et al., Univ. of Memphis Human Performance Laboratories, 2001 and 2004, Reports 1 & 2.

A preferred composition in one embodiment includes 300 mg of krill oil, 45 mg of low molecular weight HA, and 2 mg astaxanthin. The algae based oil may be substituted for the krill oil.

Astaxanthin has potent singlet oxygen quenching activity. Astaxanthin typically does not exhibit pro-oxidant activity unlike β-carotene, lutein, zeaxanthin and Vitamins A and E. Astaxanthin in some studies has been found to be about 50 times more powerful than Vitamin E, 11 times more powerful than β-carotene and three times more powerful than lutein in quenching of singlet oxygen. Astaxanthin is also well known for its ability to quench free radicals. Comparative studies have found astaxanthin to be 65 times more powerful than Vitamin C, 54 times more powerful than β-carotene, 47 times more powerful than lutein, and 14 times more powerful than Vitamin E in free radical quenching ability.

U.S. Pat. No. 5,527,533 (the Tso patent), the disclosure which is hereby incorporated by reference in its entirety, discloses the benefits of astaxanthin for retarding and ameliorating central nervous system and eye damage. Astaxanthin crosses the blood-brain-retina barrier and this can be measured by direct measurement of retinal astaxanthin concentrations. Thus, Tso demonstrated protection from photon induced damage of photo-receptors, ganglion and neuronal cell damage.

Studies have shown that HA binds to the surface of dendritic cells ("DC's") and stimulated T-cells. Blockade of the CD44-HA interaction leads to impaired T-Cell activation both in vitro and in vivo. Studies have shown that in cancer cell lines, LMWtHA fragments specifically induce nitric oxide synthase in dendritic cells. In DC's, NO expression caused dendritic cell apoptosis (cell death). DC's are essential T-cell activators which function by presenting antigens to T-cells, thus apoptosis of DC's may short circuit the adaptive immune system response. This effect was clearly CD44 dependent because pretreatment of DC's with anti-CD44 monoclonal antibodies blocked the NO mediated induction of DC apoptosis. It appears that low molecular weight HA fragments interrupt the normal course of the well known T-cell mediated adaptive immune system response. CD44 is a glycoprotein responsible in part for lymphocyte activation (also known as T-cell activation) and is known to specifically bind to HA. On the other hand as previously discussed low molecular weight HA fragments appear to up-regulate the innate immune response, particularly in chronic inflammatory conditions where the innate immune system may in some way be compromised.

Support for such teachings can be found in:
1) Mummert et al., J. of Immunol. 169, 4322-4331;
2) Termeer et al., Trends in Immunology, Vol. 24, March 2003;
3) Yang et al., Cancer Res. 62, 2583-2591; and
4) KcKee et al., J. Biol. Chem. 272, 8013-8018.

Additional information can be found in the following references: Ghosh P. Guidolin D. Semin Arthritis Rheum., 2002 August; 32(1):10-37; and P. Rooney, M. Wang, P. Kumar and S. Kumar, Journal of Cell Science 105, 213-218 (1993).

As noted before, krill oil is typically produced from Antarctic krill (euphausia superba), which is a zooplankton (base of food chain). It is one of the most abundant marine biomass of about 500 million tons according to some estimates. Antarctic krill breeds in the pure uncontaminated deep sea waters. It is a non-exploited marine biomass and the catch per year is less than or equal to about 0.02% according to some estimates. Because krill is harvested in large amounts and world supply of krill is being depleted, substitutes for krill such as other marine based oils, including algae based oils, are now being studied, developed and used.

It is believed that krill oil or other marine based oils, such as algae based oils, have an oil based phospholipid bound EPA and DHA uptake into cellular membranes that is far more efficient than triacylglyercide bound EPA and DHA since liver conversion of triacylglycerides is itself inefficient and because phospholipid bound EPA and DHA can be transported into the blood stream via the lymphatic system, thus, avoiding liver breakdown. In addition, krill and algae based oil consumption does not produce the burp-back observed with fish oil based products. Because of this burp-back feature of fish oils, it has been found that approximately 50% of all consumers who try fish oil never buy it again. Some algae based oils have EPA conjugated with phospholipid and glycolipid polar lipids, making the EPA uptake even more efficient.

Astaxanthin has an excellent safety record. A conducted study obtained the results as follows:
Oral LD 50: 600 mg/kg (rats);
NOAEL: 465 mg/kg (rats); or
Serum Pharmacokinetics: Stewart et al. 2008
1) $T_{1/2}$: 16 hours;
2) $T_{max}$: 8 hours;
3) $C_{max}$: 65 µg/L.

At eight weeks of supplementation at 6 mg per day, there was no negative effect in healthy adults. Spiller et al. 2003.

In accordance with one non-limiting example, astaxanthin has three prime sources. 3 mg astaxanthin per 240 g serving of non-farmed raised salmon or a 1% to 12% astaxanthin oleoresin or 1.5-2.5% beadlet derived from microalgae. Further verification is reflected in Lee et al., Molecules and Cells 16(1): 97-105, 2003; Ohgami et al., Investigative Ophthalmology and Visual Science 44(6): 2694-2701, 2003; Spiller et al., J. of the American College of Nutrition 21(5): October 2002; and Fry et al., University of Memphis, Human Performance Laboratories, 2001 and 2004, Reports 1 and 2.

Many beneficial and synergistic effects are now being reported herein have been observed when krill or algae based oil is used in combination with other active ingredients. More particularly, the current composition has krill or algae based oil in combination with astaxanthin and low molecular weight polymers of hyaluronic acid or sodium hyaluronate in preferably an oral dosage form for the control of joint pain range of motion and stiffness. It should be understood that different proportions of the composition components and their percentages can be used depending on end use applications and other environmental and physiological factors when treating a patient.

In accordance with a non-limiting example, the composition and method treats and alleviates symptoms of non-disease state joint pain and may be used to treat and alleviate symptoms of osteoarthritis and/or rheumatoid arthritis in a patient by administering a therapeutic amount of the composition, including the krill oil or other algae based oil in combination with astaxanthin and low molecular weight polymers of hyaluronic acid or sodium hyaluronate (hyaluronan) in an oral dosage form, preferably low molecular weight polymers. The krill oil alone, in one example, is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous.

In another example, the krill oil includes at least 15% EPA and 9% DHA, of which not less than 45% are in the form of phospholipids. The composition can be delivered advantageously for therapeutic results with 1-4000 mg of oil, krill or algae based oil, delivered per daily dose. In another example, 0.1-50 mg astaxanthin are supplemented to the oil per daily dose. The algae based oils may be substituted for the krill oil, but the composition of the algae based oils and their fatty acid profile varies from the fatty acid profiles of krill oil as explained below and shown in the tables. It is possible to also use wax esters and omega-3 salts and ethyl esters.

The astaxanthin is preferably derived from *Haematococcus pluvialis* algae, *Pfaffia*, krill, or by synthetic routes, in the free diol, monoester or diester form at a daily dose of 0.5-8 mg in one example. The polymers of hyaluronic acid or sodium hyaluronate (hyaluronan) can be derived from microbial fermentation or animal tissue. About 1-500 mg of hyaluronan can be delivered per daily dose and preferably between 10 and 70 mgs/dose. The hyaluronan is micro- or nano-dispersed within the composition in one preferred example. In another example, the hyaluronic acid is derived from a bio-fermenation process and has a molecular weight between 0.5 and 100 kilodaltons (kDa), and in another example, up to 300 kDa or 320 kDa or thereabouts, and in another example, from 0.5 to 230 kDa as low molecular weight hyaluronic acid or hyaluronan. In another example, the polymers of hyaluronic acid or sodium hyaluronate (hyaluronan) are derived from microbial fermentation or animal tissue.

The composition may also include a natural or synthetic cyclooxygenase-1 or -2 inhibitor comprising for example aspirin, acetaminophen, steroids, prednisone, or NSAIDs. The composition may also include a gamma-linoleic acid rich oil comprising Borage (*Borago officinalis* L.) or Safflower (*Carthamus tinctorius* L.), which delivers a metabolic precursor to $PGE_1$ synthesis.

The composition may also include an n-3 (omega-3) fatty acid rich oil derived from fish oil, algae oil, flax seed oil, or chic seed oil and the n-3 fatty acid comprises alpha-linolenic, stearidonic, eicosapentaenoic or docosapentaenoic acid. In one example composition as noted before, the algae based oil is used instead of krill oil. Hydrolyzed or unhydrolyzed collagen and elastin derived from eggshell membranes can also be advantageously added. The composition may also include anti-inflammatory and/or natural joint health promoting compounds comprising at least one of preparations of green lipped mussel (*Perna canaliculus*), *Boswellia serrate*, turmeric (*Curcuma longa*), stinging nettle (*Urtica dioica*), Andrographis, Cat's claw (*Uncaria tomentosa*), bromelain, methylsulfonylmethane (MSM), chondroitin sulfate, glucosamine sulfate, s-adenosyl-methionine, proanthocyanidins, procyanidins or flavonoids. The composition may include naturally-derived and synthetic antioxidants that are added to retard degradation of fatty acids and astaxanthin.

Different compositions may use different ingredients in combination with the krill or other algae based oil, the astaxanthin and hyaluronate and be combined with different ingredients and supplemental compositions for more specific purposes.

As noted above, algae based oil is used and substituted for the krill oil in an example. This algae based oil may be substituted for krill oil and provide an algae sourced EPA or an EPA/DHA based oil in which oils are present in phospholipid and glycerolipid forms, as glycolipids. Different algae based oils derived from different microalgae may be used. One preferred example algae based oil has the EPA titre higher than the DHA as compared to a class of omega-3's from fish oils that are triacylglycerides. These algae based oils are rich in EPA and in the phospholipid and glycolipid forms. An example marine based algae oil is produced by Parry Nutraceuticals as a division of EID Parry (India) Ltd. as an omega-3 (EPA) oil.

The following first table shows the specification of an algae based oil as manufactured by Parry Nutraceuticals identified above, followed by a second table for a fatty acid profile chart of that algae based oil. A third table is a comparative chart of the fatty acid profiles for non-algae based oils. These charts show that the algae based oil has a high EPA content of phospholipids and glycolipids.

| SPECIFICATION: ALGAE BASED OIL | | | |
|---|---|---|---|
| PARAMETERS | SPECIFICATION | SOP. NO | TEST METHOD/ REFERENCE |
| Physical Properties | | | |
| Appearance | Viscous oil | QA - 88 | In house |
| Color | Brownish black | QA - 88 | In house |
| Odor | Characteristic | QA - 88 | In house |
| Taste | Characteristic | QA - 88 | In house |
| General Composition | | | |
| Loss on drying (%) | 2.0-3.0 | QA - 038 | USP <731> Loss on drying |
| Ash (%) | 0.5-1.0 | QA - 080 | AOAC Official Method 942.05, 16th Edition |
| Protein (%) | 1.0-2.0 | QA - 021 | AOAC Official method 978.04, 16th Edn. |
| Carbohydrate (%) | 1.0-2.0 | | AOAC 18th Edn 2006/By Difference |
| Residual Solvent (ppm) (as Ethyl Acetate) (as Acetone) | NMT 100 NMT 30 | QA - 074 | GC - Head Space, USP <467> |
| Lipid Composition | | | |
| Total Lipid (%) | 92.0-95.0 | QA - 86 | AOAC official method 933.08 |
| Chlorophyll (%) | NMT 1.50 | QA - 078 | Jeffrey & Humphrey (1975) - Photosynthetic pigments of Algae (1989) |
| Total carotenoids (%) | NMT 1.50 | QA - 85 | By JHFA method-1986 |
| Total Unsaponifiables (%) | NMT 12.0 | QA - 086 | AOAC official method 933.08 |
| Omega 3 [EPA + DHA] - % w/w | NLT 15.00 | QA - 087 | In House method |
| Total Omega 3 (% w/w) | NLT 17.00 | | |
| Total Omega 6 (% w/w) | NMT 5.00 | | |
| Total EFA (% w/w) | NLT 20. | | |
| Lipid percentage | | | |
| Triglycerides | 15-20% | | |
| Phospholipids | 5-10% | | |
| Glycolipids | 35-40% | | |
| Free fatty acids | 15-20% | | |

SPECIFICATION: ALGAE BASED OIL

| PARAMETERS | SPECIFICATION | SOP. NO | TEST METHOD/REFERENCE |
|---|---|---|---|
| Microbial parameters | | | |
| Standard Plate Count (cfu/1 g) | NMT 1,000 | QA - 039 | AOAC, 1995, Chapter 17 |
| Yeast & Mold (cfu/1 g) | NMT 100 | | |
| Coli forms (/10 g) | Negative | | |
| E. Coli (/10 g) | Negative | | |
| Staphylococcus (/10 g) | Negative | | |
| Salmonella (/10 g) | Negative | | |
| Fatty acid profile (Area %) | | | |
| Myristic acid [14.0] | NLT 4.0 | QA - 086 & 087 | In House GC method |
| Palmiltic acid [16:0] | NLT 16.0 | | |
| Palmito oleic acid [16:1, n-9] | NLT 12.0 | | |
| Hexadecadienoic acid [16:2, n-4] | NLT 4.0 | | |
| Hexadecatrienoic acid [16:3, n-4] | NLT 12.0 | | |
| Stearic acid [18:0] | NLT 0.10 | | |
| Oleic acid [18:1] | NLT 1.0 | | |
| Linoleic acid [18:2, n-6] - LA | NLT 1.0 | | |
| AlphaLinolenic acid [18:3, n-3] - ALA | NLT 0.50 | | |
| Stearidonic acid [18:4, n-3] - SA | NLT 0.10 | | |
| Arachidonic Acid [20:4, n-6] - AA | NLT 0.25 | | |
| Eicosapentaenoic acid [20:5, n-3] | NLT 15.0 | | |
| Decosahexaenoic acid [20:6, n-3] | NLT 1.5 | | |
| Heavy Metals | | | |
| Lead (ppm.) | NMT 1.0 | External lab reports | AOAC 18th Edn: 2006 By ICPMS |
| Arsenic (ppm) | NMT 0.5 | | |
| Cadmium (ppm) | NMT 0.05 | | |
| Mercury (ppm) | NMT 0.05 | | |

Safety: Safe for the intended use
Shelf life: 24 months from the date of manufacture
Stability: Stable in unopen conditions
Storage: Store in a cool, dry place away from sunlight, flush container with Nitrogen after use
Documentation: Every Batch of shipment carries COA
Packing: 1 kg, 5 kg, and 20 kg food grade containers

FATTY ACID PROFILE CHART ALGAE BASED OIL

| FATTY ACID | ALGAE BASED OMEGA-3 (EPA) OIL |
|---|---|
| Total fatty acid, gm/100 gm of oil | 75 gm |
| Fatty acid [% of total fatty acid] | |
| Myristic acid [14:0] | 6.87 |
| Pentadecanoic acid [15:0] | NA |
| Palmitic acid [16:0] | 20.12 |
| Palmito oleic acid [16:1, ω-9] | 18.75 |
| Hexadeca dienoic acid [16:2, ω-4] | 6.84 |
| Hexadeca trienoic acid [16:4, ω-4] | 12.54 |
| Heptadecanoic acid [17:0] | NA |
| Stearic acid [18:0] | 0.68 |
| Oleic acid [18:1, ω-9] | 3.56 |
| Linoleic acid [18:2, ω-6] | 2.68 |
| Alpha linolenic acid [18:3, ω-3] | 3.73 |
| Gamma linolenic acid [18:3, ω-6] | NA |
| Stearidoni acid [18:4, ω-3] | 0.33 |
| Arachidonic acid [20:4, ω-6] | 0.97 |
| Eicosapentaenoic acid [20:5, ω-3] EPA | 23.00 |
| Docosapentaenoic acid [22:5, ω-3] DHA | NA |
| Docosahexaenoic acid [22:6, ω-3] DHA | 3.26 |
| others | 3.54 |
| EPA/DHA [gm/100 gm oil] | 15.75 |
| Total ω-3 fatty acids [gm/100 gm oil] | 18.20 |
| LIPD CLASS DETAILS [gm/100 gm oil] | |
| Unsaponifiables [carotenoids, chlorophyll, sterol, fatty alcohol etc.,] | 12 |
| Free fatty acids | 20 |
| Triglydcerides | 20 |
| Phospholipids | 10 |
| Glycolipids | 38 |
| Total | 100 |
| STABILITY [months] | 24 |

FATTY ACID PROFILE - COMPARATIVE CHART
NON-ALGAE BASED OILS

| FATTY ACID | FISH OIL MAXEPA | KRILL OIL | MARTEK OIL |
|---|---|---|---|
| Total fatty acid, gm/100 gm of oil | 95 gm | 70-80 gm | 95 gm |
| Fatty acid [% of total fatty acid] | | | |
| Myristic acid [14:0] | 8.68 | 11.09 | 11.47 |
| Pentadecanoic acid [15:0] | NA | NA | NA |
| Palmitic acid [16:0] | 20.35 | 22.95 | 26.36 |
| Palmito oleic acid [16:1, ω-9] | 11.25 | 6.63 | NA |
| Hexadeca dienoic acid [16:2, ω-4] | NA | NA | NA |
| Hexadeca trienoic acid [16:4, ω-4] | NA | NA | NA |
| Heptadecarioic acid [17:0] | NA | NA | NA |
| Stearic acid [18:0] | 4.67 | 1.02 | 0.50 |
| Oleic acid [18:1, ω-9] | 13.07 | 17.93 | 1.50 |
| Linoleic acid [18:2, ω-6] | 1.28 | 0.14 | 0.61 |
| Alpha linolenic acid [18:3, ω-3] | 0.33 | 2.11 | 0.40 |
| Gamma linolenic acid [18:3, ω-6] | NA | NA | NA |
| Stearidoni acid [18:4, ω-3] | 1.69 | 7.01 | 0.33 |
| Arachidonic acid [20:4, ω-6] | 0.50 | NA | NA |
| Eicosa pentaenoic acid [20:5, ω-3] EPA | 20.31 | 19.04 | 1.0 |
| Docosa pentaenoic acid [22:5, ω-3] DHA | NA | NA | 15.21 |
| Docosa hexaenoic acid [22:6, ω-3] DHA | 13.34 | 11.94 | 42.65 |
| others | 4.53 | 0.14 | NA |
| EPA/DHA [gm/100 gm oil] | 31.96 | 21.68 | 41.46 |
| Total ω-3 fatty acids [gm/100 gm oil] | 33.85 | 28.00 | 41.60 |
| LIPD CLASS DETAILS [gm/100 gm oil] | | | |
| Unsaponifiables [carotenoids, chlorophyll, sterol, fatty alcohol etc.,] | 5 | 5 | 5 |
| Free fatty acids | 0.5 | 30 | 0.5 |
| Triglydcerides | 94.5 | 25 | 94.5 |
| Phospholipids | Nil | 40 | Nil |
| Glycolipids | Nil | Nil | Nil |
| Total | 100 | 100 | 100 |
| STABILITY [months] | 12 | 24 | 6 |

Different types of marine based algae oils may be used, including *nannochloropsis oculata* as a source of EPA. Another algae that may be used is *thalassiosira weissflogii* such as described in U.S. Pat. No. 8,030,037 assigned to the above-mentioned Parry Nutraceuticals, a Division of EID Parry (India) Ltd., the disclosure which is hereby incorporated by reference in its entirety. Other types of algae as disclosed include *chaetoceros* sp. or *prymnesiophyta* or green algae such as *chlorophyta* and other microalgae that are *diamons tiatoms*. The *chlorophyta* could be *tetraselmis* sp. and include *prymnesiophyta* such as the class prymnesiophyceae and such as the order *isochrysales* and more specifically, *isochrysis* sp. or *pavlova* sp.

There are many other algae species that can be used to produce EPA and DHA as an algae based oil whether marine based or not to be used in accordance with a non-limiting example. In some cases, the isolation of the phospholipid and glycolipid bound EPA and DHA based oils may require manipulation of the algae species growth cycle.

Other algae/fungi phospholipid/glycolipid sources include: *grateloupia turuturu; porphyridium cruentum; monodus subterraneus; phaeodactylum tricornutum; isochrysis galbana; navicula* sp.; *pythium irregule; nannochloropsis* sp.; and *nitzschia* sp.

Details regarding *grateloupia turuturu* are disclosed in the article entitled, "*Grateloupia Turuturu* (Halymeniaceae, *Skeletonema costatum* Rhodophyta) is the Correct Name of the Non-Native Species in the Atlantic Known as *Grateloupia Doryphora*," Eur. J. Phycol. (2002), 37: 349-359, as authored by Brigitte Gavio and Suzanne Fredericq, the disclosure which is incorporated by reference in its entirety.

*Porphyridium cruentum* is a red algae in the family porphyridiophyceae and also termed *rhodophyta* and is used as a source for fatty acids, lipids, cell-wall polysaccharides and pigments. The polysaccharides of this species are sulphated. Some *porphyridium cruentum* biomass contains carbohydrates of up to 57%.

*Monodus subterraneus* is described in an article entitled, "Biosynthesis of Eicosapentaenoic Acid (EPA) in the Fresh Water *Eustigmatophyte Monodus Subterraneus* (Eustigmatophyceae)," J. Phycol, 38, 745-756 (2002), authored by Goldberg, Shayakhmetova, and Cohen, the disclosure which is incorporated by reference in its entirety. The biosynthesis of PUFAs from algae is complicated and the biosynthesis from this algae is described in that article.

*Phaeodactylum tricornutum* is a diatom and unlike most diatoms, it can grow in the absence of silicon and the biogenesis of silicified frustules is facultative.

*Isochrysis galbana* is a microalgae and used in the bivalve aquaculture industry.

*Navicula* sp. is a boat-shaped algae and is a diatom. *Pythium irregule* is a soilborne pathogen found on plant hosts.

*Nannochloropsis* sp. occurs in a marine environment, but also occurs in fresh and brackish water. The species are small, nonmotile spheres that do not express any distinct morphological feature. These algae have chlorophyll A and lack chlorophyll B and C. They can build high concentrations of pigment such as astaxanthin, zeaxanthin and canthaxinthin. They are about 2-3 micrometers in diameter. They may accumulate high levels of polyunsaturated fatty acids.

*Nitzschia* sp. is a pinnate marine diatom and usually found in colder waters and associated with both Arctic and Antarctic polar sea ice where it is a dominant diatom. It produces a neurotoxin known as domoic acid which is responsible for amnesic shell fish poisoning. It may grow exponentially at temperatures between –4 and –6 degrees C. It may be processed to form and extrapolate the fatty acids.

As a source of polyunsaturated fatty acids, microalgae competes with other micro-organisms such as fungi and bacteria. There may be some bacterial strains that could be an EPA source, but microalgae has been found to be a more adequate and readily available source. Microalgae is a good source of oil and EPA when derived from *phaeodactylum, isochrysis* and *monodus*. The microalgae *phaeodactylum tricornutum* produces a high proportion of EPA. Other different strains and species of microalgae, fungi and possibly bacteria that can be used to source EPA include the following:

I. Diatoms
   *Asterionella japonica*
   *Bidulphia sinensis*
   *Chaetoceros septentrionale*
   *Lauderia borealis*
   *Navicula biskanteri*
   *Navicula laevis* (heterotrof.)
   *Navicula laevis*
   *Navicula incerta*
   *Stauroneis amphioxys*
   *Navicula pellicuolsa*
   *Bidulphia aurtia*
   *Nitzschia alba*
   *Nitzschia chosterium*
   *Phaeodactylum tricornutum*
   *Phaeodactylum tricornutum*

II. Chrysophyceae
  Pseudopedinella sp.
  Cricosphaera elongate
III. Eustigmatophyceae
  Monodus subterraneus
  Nannochloropsis
IV. Prymnesiophyceae
  Rodela violacea 115.79
  Porphyry. Cruentum 1380.Id
V. Prasinophyceae
  Pavlova saline
VI. Dinophyceae
  Cochlodinium heteroloblatum
  Cryptecodinium cohnii
  Gonyaulax catenella
  Gyrodinium cohnii
  Prorocentrum minimum
VII. Other Microalgae
  Chlorella minutissima
  Isochrysis galbana ALII4
  Phaeodactylum tricornutum WT
  Porphyridium cruentum
  Monodus subterraneus
VIII. Fungi
  Mortierella alpine
  Mortierella alpine IS-4
  Pythium irregulars
IX. Bacteria
  SCRC-2738

Different microalgae may be used to form the algae based oil comprising glycolipids and phospholipids and at least EPA and/or EPA/DHA. Examples include: Chlorophyta, Cyanophyta (Cyanobacteria), and Heterokontophyta. The microalgae may be from one of the following classes: Bacillariophyceae, Eustigmatophyceae, and Chrysophyceae. The microalgae may be from one of the following genera: *Nannochloropsis*, *Chlorella*, *Dunaliella*, *Scenedesmus*, *Selenastrum*, *Oscillatoria*, *Phormidium*, *Spirulina*, *Amphora*, and *Ochromonas*.

Other non-limiting examples of microalgae species that may be used include: *Achnanthes orientalis*, *Agmenellum* spp., *Amphiprora hyaline*, *Amphora coffeiformis*, *Amphora coffeiformis* var. *linea*, *Amphora coffeiformis* var. *punctata*, *Amphora coffeiformis* var. *taylori*, *Amphora coffeiformis* var. *tenuis*, *Amphora delicatissima*, *Amphora delicatissima* var. *capitata*, *Amphora* sp., *Anabaena*, *Ankistrodesmus*, *Ankistrodesmus falcatus*, *Boekelovia hooglandii*, *Borodinella* sp., *Botryococcus braunii*, *Botryococcus sudeticus*, *Bracteococcus minor*, *Bracteococcus medionucleatus*, *Carteria*, *Chaetoceros gracilis*, *Chaetoceros muelleri*, *Chaetoceros muelleri* var. *subsalsum*, *Chaetoceros* sp., *Chlamydomas perigranulata*, *Chlorella anitrata*, *Chlorella antarctica*, *Chlorella aureoviridis*, *Chlorella candida*, *Chlorella capsulate*, *Chlorella desiccate*, *Chlorella ellipsoidea*, *Chlorella emersonii*, *Chlorella fusca*, *Chlorella fusca* var. *vacuolata*, *Chlorella glucotropha*, *Chlorella infusionum*, *Chlorella infusionum* var. *actophila*, *Chlorella infusionum* var. *auxenophila*, *Chlorella kessleri*, *Chlorella lobophora*, *Chlorella luteoviridis*, *Chlorella luteoviridis* var. *aureoviridis*, *Chlorella luteoviridis* var. *lutescens*, *Chlorella miniata*, *Chlorella minutissima*, *Chlorella mutabilis*, *Chlorella nocturna*, *Chlorella ovalis*, *Chlorella parva*, *Chlorella photophila*, *Chlorella pringsheimii*, *Chlorella protothecoides*, *Chlorella protothecoides* var. *acidicola*, *Chlorella regularis*, *Chlorella regularis* var. *minima*, *Chlorella regularis* var. *umbricata*, *Chlorella reisiglii*, *Chlorella saccharophila*, *Chlorella saccharophila* var. *ellipsoidea*, *Chlorella saline*, *Chlorella simplex*, *Chlorella sorokiniana*, *Chlorella* sp., *Chlorella sphaerica*, *Chlorella stigmatophora*, *Chlorella vanniellii*, *Chlorella vulgaris*, *Chlorella vulgaris* fo. *tertia*, *Chlorella vulgaris* var. *autotrophica*, *Chlorella vulgaris* var. *viridis*, *Chlorella vulgaris* var. *vulgaris*, *Chlorella vulgaris* var. *vulgaris* fo. *tertia*, *Chlorella vulgaris* var. *vulgaris* fo. *viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cricosphaera* sp., *Crypthecodinium cohnii*, *Cryptomonas* sp., *Cyclotella cryptica*, *Cyclotella meneghiniana*, *Cyclotella* sp., *Dunaliella* sp., *Dunaliella bardawil*, *Dunaliella bioculata*, *Dunaliella granulate*, *Dunaliella maritime*, *Dunaliella minute*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertiolecta*, *Eremosphaera viridis*, *Eremosphaera* sp., *Effipsoidon* sp., *Euglena* spp., *Franceia* sp., *Fragilaria crotonensis*, *Fragilaria* sp., *Gleocapsa* sp., *Gloeothamnion* sp., *Haematococcus pluvialis*, *Hymenomonas* sp., *Isochrysis* aff. *galbana*, *Isochrysis galbana*, *Lepocinclis*, *Micractinium*, *Micractinium*, *Monoraphidium minutum*, *Monoraphidium* sp., *Nannochloris* sp., *Nannochloropsis sauna*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia closterium*, *Nitzschia communis*, *Nitzschia dissipate*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Parachlorella kessleri*, *Pascheria acidophila*, *Pavlova* sp., *Phaeodactylum tricomutum*, *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chrysophyte*, *Scenedesmus armatus*, *Schizochytrium*, *Spirogyra*, *Spirulina platensis*, *Stichococcus* sp., *Synechococcus* sp., *Synechocystisf*, *Tagetes erects*, *Tagetes patula*, *Tetreedron*, *Tetraselmis* sp., *Tetraselmis suecica*, *Thalassiosira* and *Viridiella fridericiana*. Preferably, the microalgae are autotrophic.

It is also possible to form the oil comprising glycolipids and phospholipids and at least EPA from genetically modified yeast. Non-limiting examples of yeast that can be used include *Cryptococcus curvatus*, *Cryptococcus terricolus*, *Lipomyces starkeyi*, *Lipomyces lipofer*, *Endomycopsis vernalis*, *Rhodotorula glutinis*, *Rhodotorula gracilis*, *Candida* 107, *Saccharomyces paradoxus*, *Saccharomyces mikatae*, *Saccharomyces bayanus*, *Saccharomyces cerevisiae*, any *Cryptococcus*, *C. neoformans*, *C. bogoriensis*, *Yarrowia lipolytica*, *Apiotrichum curvatura*, *T. bombicola*, *T. apicola*, *T. petrophilum*, *C. tropicalis*, *C. lipolytica*, and *Candida albicans*. It is even possible to use a biomass as a wild type or genetically modified fungus. Non-limiting examples of fungi that may be used include *Mortierella*, *Mortierrla vinacea*, *Mortierella alpine*, *Pythium debaryanum*, *Mucor circinelloides*, *Aspergillus ochraceus*, *Aspergillus terreus*, *Pennicillium iilacinum*, *Hensenulo*, *Chaetomium*, *Cladosporium*, *Malbranchea*, *Rhizopus*, and *Pythium*.

It is also possible that bacteria may be used that includes lipids, proteins, and carbohydrates, whether naturally occurring or by genetic engineering. Non-limiting examples of bacteria include: *Escherichia coli, Acinetobacter* sp. any actinomycete, *Mycobacterium tuberculosis*, any streptomycete, *Acinetobacter calcoaceticus, P. aeruginosa, Pseudomonas* sp., *R. erythropolis, N. erthopolis, Mycobacterium* sp., B., *U. zeae, U. maydis, B. lichenformis, S. marcescens, P. fluorescens, B. subtilis, B. brevis, B. polmyma, C. lepus, N. erthropolis, T. thiooxidans, D. polymorphis, P. aeruginosa* and *Rhodococcus opacus*.

Possible algae sourced, EPA/DHA based oils that are derived from an algae and contain glycol and phospholipid bound EPA and/or EPA/DHA and may include a significant amount of free fatty acids, triglycerides and phospholipids and glycolipids in the range of 35-40% or more of total lipids are disclosed in the treatise "Chemicals from Microalgae" as edited by Zvi Cohen, CRC Press, 1999. Reference is also made to a study in men that have been given a single dose of oil from a polar-lipid rich oil from the algae *nannochloropis oculata* as a source of EPA and described in the article entitled, "Acute Appearance of Fatty Acids in Human Plasma—A Comparative Study Between Polar-Lipid Rich Oil from the Microalgae *Nannochloropis Oculata* in Krill Oil in Healthy Young Males," as published in Lipids in Health and Disease, 2013, 12:102 by Kagan et al. The EPA in that algae oil was higher than that of krill oil by about 25.06 to 13.63 for fatty acid composition as the percent of oil. The algae oil was provided at 1.5 grams of EPA and no DHA as compared to krill oil that was provided at 1.02 grams EPA and 0.54 grams DHA. The participants consumed both oils in random order and separated by seven days and the blood samples were collected before breakfast and at several time points up to 10 hours after taking the oils.

The researchers determined that the algae based oil had a greater concentration of EPA and plasma than krill oil with the EPA concentration higher with the algae based oil at 5, 6, 8 and 10 hours (P<0.05) intended to be higher at 4 hours (P=0.094). The maximum concentration (CMAX) of EPA was higher with algae oil than with krill oil (P=0.010). The maximum change in concentration of EPA from its fasting concentration was higher than with krill oil (P=0.006). The area under the concentration curve (AUC) and the incremental AUC (IAUC) was greater (P=0.020 and P=0.006). This difference may relate to the different chemical composition and possibly the presence of the glycolipids where the presence of DHA in krill oil limits the incorporation of EPA into plasma lipids. Also, the n-3 polyunsaturated fatty acids within glycolipids as found in the algae oil, but not in a krill oil, may be an effective system for delivering EPA to humans.

The incorporated by reference '037 patent describes the benefit of using an algae based oil, and more particularly, a marine based algae oil and discloses different manufacturing and production techniques. Microalgae can be cultured photoautotrophically outdoors to prepare concentrated microalgae products containing Eicosapentaenoic acid (EPA) and Docosahexaenoic acid (DHA), which are the long-chain polyunsaturated fatty acids (PUFAs) found in fish oil. Both are very important for human and animal health. The concentrated microalgae products as disclosed in the '037 patent may contain EPA and DHA and lipid products containing EPA and DHA purified from microalgae. The concentrated microalgae composition may be prepared by cultivating microalgae photoautotrophically outdoors in open ponds under filtered sunlight in a continuous or batch mode and at a dilution rate of less than 35% per day. The microalgae may be harvested in the exponential phase when the cell number is increasing at a rate of at least 20% of maximal rate. In one example, the microalgae is concentrated. In another example, at least 40% by weight of lipids in the microalgae are in the form of glycodiacylglycerides, phosphodiacylglycerides, or a combination thereof and at least 5% by weight of the fatty acids are DHA, EPA, or a combination thereof.

In one example, the microalgae are *Tetraselmis* sp. cultivated at above 20° C. or in another example at above 30° C. The EPA yield in the microalgae has been found to be at least 10 mg/liter culture. The microalgae can be *Isochrysis* sp. or *Pavlova* sp. in another example, or are *Thalassiosira* sp. or *Chaetecoros* sp. The microalgae may be different diatoms and are cultivated photoautotrophically outdoors in open ponds for at least 14 days under filtered sunlight and at least 20% by weight of the fatty acids are EPA.

The use of this algae based oil overcomes the technical problems associated with the dwindling supplies of fish oil and/or Antarctic krill, which are now more difficult to harvest and obtain and use economically because these products are in high demand. A major difference between fish oils and algae based oils is their structure. Fish oils are storage lipids and are in the form of triacylgycerides. The algae based oils as lipids are a mixture of storage lipids and membrane lipids. The EPA and DHA present in algae based oils is mainly in the form of glycolipids and a small percentage is in the form of phospholipids. Glycolipids are primarily part of chloroplast membranes and phospholipids are part of cell membranes.

The '037 patent describes various methods for culturing microalgae photoautotrophically outdoors to produce EPA and DHA. One method used is filtering sunlight to reduce the light intensity on the photoautotrophic culture. Shade cloth or netting can be used for this purpose. It was determined that for most strains, the optimal solar intensity for growth, for maintaining a pure culture, and for omega-3 fatty acid accumulation was about 40,000 to 50,000 lux, approximately half of the 110,000 lux of full sunlight. Shade cloth or netting is suitable for filtering the sunlight to the desired intensity.

It is also possible to culture microalgae photoautotrophically outdoors and produce EPA and DHA by using small dilutions and a slow dilution rate of less than 40% per day, preferably less than 35% per day, more preferably from about 15% to about 30% per day. In other examples, the dilution rate is 15-40% per day or 15-35% per day, and in yet other examples, the dilution rate is 10-30%, 10-35%, or 10-40% per day. These smaller dilutions and lower dilution rates than are usually used help prevent contamination in outdoor photoautotrophic cultures. It also promotes thick culture growth that gives good DHA or EPA yield.

Another technique to successfully culture microalgae photoautotrophically outdoors and produce EPA and EPA/DHA is to harvest the microalgae in exponential phase rather than stationary phase. Harvesting in exponential phase reduces the risk of contamination in outdoor photoautotrophic cultures and has surprisingly been found to give a good yield of EPA and DHA. To drive fat accumulation in microbial cultures, the cultures are harvested in stationary phase because cells in the stationary phase tend to accumulate storage lipids. The '037 patent teaches that EPA and DHA accumulate in large amounts as membrane lipids in cultures harvested in the exponential phase. The membrane lipids containing EPA and DHA are predominantly phosphodiacylglycerides and glycodiacylglycerides, rather than the triaclyglycerides found in storage lipids. These cultures are harvested often when cell number is increasing at a rate at least 20% of the maximal rate, i.e., the maximal rate achieved at any stage during the outdoor photoautotrophic growth of the harvested culture. In specific examples, the cultures are harvested in exponential phase when cell number is increasing at a rate of at least 30%, at least 40%, or at least 50% of maximal rate. It is also possible to use recombinant DNA techniques.

The '037 patent includes several examples, which are referenced to the reader for description and teaching purposes.

EXAMPLE 1

The strain *Thalassiosira* sp. is a diatom and this strain used was isolated from Bay of Bengal, and it dominates during summer months. This example strain was isolated from seawater collected near Chemai, India, and the culture was maintained in open tubs. The particular strain was identified as *Thalassiosira weissflogii*, which is capable of growth at high temperatures (35-38° C.). The fatty acid profile was good even when the alga was grown at high temperature with 25-30% EPA (as a percentage of fatty acids).

Culturing: The lab cultures were maintained in tubs in an artificial seawater medium, under fluorescent lights (3000-4000 lux) and the temperature was maintained at 25° C. Initial expansion of the culture was done under laboratory condition in tubs. The dilution rate was 15% to 30% of the total culture volume per day. Once the volume was 40-50 liters, it was transferred to an outdoor pond. The outdoor ponds were covered with netting to control the light (40,000 to 50,000 lux). The dilution continued until the culture reached 100,000 liters volume. The culture was held in 500 square meter ponds at this time with a culture depth of 20 cm. The culture was stirred with a paddle wheel and $CO_2$ was mixed to keep the culture pH neutral. When the EPA levels in the pond reached a desirable level (10-15 mg/lit), the whole pond was harvested by filtration. The filtered biomass was washed with saltwater (15 parts per thousand concentration) and then spray dried. The mode of culturing was batch mode. The EPA productivity was 2-3 mg/lit/day. The ponds can also be run continuously for several weeks by harvesting part of the culture, recycling the filtrate into the ponds and replenishing required nutrients.

EXAMPLE 2

The strain *Tetraseimis* sp. is in the division Chlorophyta and the class Prosinophyceae or Micromanadophyceae. This strain was obtained from the Central Marine Fisheries Research Institute, India. It was isolated from the local marine habitats in India. The culture was maintained in flasks in artificial seawater medium, and expanded as described for *Thalassiosira*. With culture outdoors in open ponds as described for *Thalassiosira*, the strain gave a good lipid yield (200-300 mg/liter) and an EPA content of 6-7% of fatty acids.

EXAMPLE 3

The strain *Chaetoceros* sp. is another diatom strain obtained from the Central Marine Fisheries Research Institute, India, and isolated from local marine habitats in India. *Chaetoceros* sp. was maintained in flasks and cultivated in outdoor ponds photoautotrophically as described in Example 1. It gave similar EPA productivity and EPA content as *Thalassiosira* as described in Example 1.

EXAMPLE 4

The strain *Isochrysis* sp. is in the Prymnesiophyta, class Prymnesiophyceae, order Isochrysidales. It was obtained from the Central Marine Fisheries Research Institute, India, and isolated from local marine habitats in India. It was maintained and grown as described in Example 1. It was expanded from laboratory culture to a 50,000 liter outdoor pond culture in 14-15 days with a dilution rate of 15-30% per day. The lipid content at harvest was 100-150 mg lipids/liter. The rate of lipid production was 25-50 mg/liter/day. DHA was 10-12% of total fatty acids.

EXAMPLE 5

Harvesting and Drying: The harvesting may be done by flocculation. The commonly used flocculants include Alum with polymer and FeCl3 with or without polymer and chitosan. The concentration of flocculent will depend on the cell number in the culture before harvest. The range may vary from 100 ppm to 500 ppm. Alternatively, harvesting is done by filtration using appropriate meshes. Removal of adhered chemicals (other than salt) is accomplished by washing the cells in low salinity water.

The harvested slurry is then taken for spray drying. The slurry is sometimes encapsulated to prevent oxidation. The concentration of encapsulating agent may vary from 0.1 to 1.0% on a dry weight basis. Modified starch is a suitable encapsulating agent. The spray dryer is usually an atomizer or nozzle type. The inlet temperature ranges from 160 to 190° C. and the outlet temperature ranges from 60 to 90° C. The spray dried powder is used immediately for extraction. If storage is required, the powder is packed in aluminum laminated pouches and sealed after displacing the air by nitrogen. The packed powder is stored at ambient temperature until further use.

EXAMPLE 6

Extraction of EPA/DHA is carried out using a wet slurry or dry powder and solvents, which include hexane, ethanol, methanol, acetone, ethyl acetate, isopropanol and cyclohexane and water, either alone or in combination of two solvents. The solvent to biomass ratio depends on the starting material. If it is a slurry, the ratio is 1:2 to 1:10. With a spray dried powder, on the other hand, the ratio is 1:4 to 1:30. The extraction is carried out in an extraction vessel under inert atmosphere, with temperature ranges from 25 to 60° C. and with time varying from one hour to 10 hours. Solvent addition is made one time or in parts based on the lipid level in the cells.

After extraction of crude lipid, the mixture is passed through a centrifuge or filtration system to remove the cell debris. The lipid in the filtrate is concentrated by removing the solvent by distillation, which is carried out under vacuum. The resulting product is a crude lipid extract, which contains approximately 10% omega-3 fatty acid (EPA/DHA). The extract can be used as it is or purified further to enrich the omega-3 fatty acids. Further purification may involve removal of unsaponifiables such as pigments, sterols and their esters.

The algae based oil composition may be used for different purposes as described. A pharmaceutically acceptable composition comprises a krill or algae based oil in combination with astaxanthin and hyaluronate optionally combined with one or more ingredients including but not limited to glucosamine sulfate, chondroitin sulfate, collagen, methylsulfonmethane, a gamma-linoleic acid or omega-3 fatty acid rich oil a cyclooxgenase inhibitor or a lipogenase inhibitor for the treatment of symptoms related to non-disease joint pain and/or joint diseases, including but not limited to osteoarthritis and rheumatoid arthritis.

In yet another example, a dietary supplement acceptable composition comprises a krill or algae based oil in combination with astaxanthin and hyaluronate optionally combined one or more ingredients, including but not limited to, glucosamine sulfate, chondroitin sulfate, collagen, methylsulfonmethane, a gamma-linoleic acid or omega-3 fatty acid rich oil a cyclooxygenase inhibitor or a lipoxygenase inhibitor for the treatment of symptoms related to non-disease joint pain and/or joint diseases, including but not limited to osteoarthritis and rheumatoid arthritis.

In yet another example, a medical food acceptable composition comprises a krill or algae based oil in combination with astaxanthin and hyaluronate and optionally combined with one or more ingredients including glucosamine sulfate, chondroitin sulfate, collagen, methylsulfonmethane, a gamma-linoleic acid or omega-3 fatty acid rich oil, a cyclooxygenase inhibitor or a lipoxygenase inhibitor for the treatment of symptoms related to non-disease joint pain and/or joint diseases, including but not limited to osteoarthritis and rheumatoid arthritis.

In still another example, a composition is formulated in a therapeutic amount to treat and alleviate symptoms of non-disease joint pain and/or joint diseases, including osteoarthritis and/or rheumatoid arthritis, wherein the composition includes a krill or algae based oil in combination with astaxanthin and polymers of hyaluronic acid or sodium hyaluronate (hyaluronan) in an oral dosage form. This composition includes other active constituents as explained and identified above relative to the method and composition.

The composition oil, whether from krill or algae based oil, is used with the HA, such as the low molecular weight HA, and astaxanthin to treat non-disease joint pain in one example, but can be used to treat osteoarthritis. Osteoarthritis (OA) is the most prevalent form of arthritis and is a disease in which the cartilage that acts as a cushion between the bones in joints begins to wear away causing bone on bone joint swelling and joint pain. It is characterized by degeneration of articular cartilage along with peri-articular bone response. It affects both sexes, mainly in the fourth and fifth decades of life. The knee joint is most commonly affected joint. At present the management is by pharmacological and non-pharmacological therapy. Corrective surgical therapy and or joint replacement therapy in some cases may not be possible.

Traditional treatments for Osteoarthritis involve the use of analgesics, non-steroidal anti-inflammatory drugs (NSAIDs) or cyclooxygenase-2 specific (COX-2) NSAIDs alone or in combination. Advances in recombinant protein synthesis also provide relief from the symptoms of OA and RH. Steroid or high molecular weight hyaluronic acid injections have also been used with some success however these therapies have well known deleterious side effects.

Many of these treatments alone have shown limited effectiveness in clinical trials. To avoid the cardiac risks and gastrointestinal issues associated with traditional OA treatments (particularly with long term use), many patients have turned to complimentary and alternative medicines (CAMs) such as dietary supplements. Glucosamine and chondroitin alone or in combination, are widely marketed as dietary supplements to treat joint pain due to OA. Two major clinical trials on glucosamine and chondroitin (The GAIT Study) failed to show any significant improvement in WOMAC score over placebo except in the highest quartile of patients studied. Because of their limited effectiveness, the search for additional CAMs to treat OA continues (see for example Ruff et al., Eggshell Membrane in the Treatment of Pain and Stiffness from Osteoarthritis of the Knee: A Randomized, Multicenter, Double-Blind, Placebo-Controlled Clinical Study, Clin. Rheumatol (2009) 28:907-914).

It is also possible to use a pure diol of the S, S'astaxanthin. It is possible to use that pure diol in combination with the EPA rich algae based oil as described above and which is admixed with either astaxanthin derived from *Haematococcus pluvialis* or the free dial form in substantially pure S,S' enantiomer form. It is possible to add synthetically derived mixed enantiomers of the dial as a product that is sold as a fish food in one non-limiting example. The diol of the S, S'astaxanthin is possible because in both cases of krill oil and possibly the algae based oil and Hp derived, there are principally diesters and monoesters respectively with very little diol, which is insoluble. Some research indicates that it may be many times more bioavailable than either the monoester or diester form. It is possible to asymmetrically synthesize the S,S' pure diol. Despite the pure diol's poor solubility in some examples, there may be an active transport mechanism related to its bioavailability, or conversely, that only in the diol form is the monoester or diester forms transferred from the intestines to the blood. The phospholipid or glycolipid based product presenting EPA and/or DHA along with the added astaxanthin in its various forms and especially the S,S' enantiomeric form in principally monoester form from *Haematococcus pluvialis* or pure diol form from asymmetric synthesis could be viable. Thus, it is possible to combine it with the algae derived glycol and phospholipid based EPA rich oil.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A dietary supplement composition formulated in a therapeutic amount to treat and alleviate symptoms of joint pain in a patient wherein the composition includes an algae based oil comprising glycolipids and phospholipids and Eicosapentaenoic (EPA) fatty acids in combination with astaxanthin and pro-inflammatory low molecular weight sodium hyaluronate fragments having a molecular weight of 0.5 to 300 kilodaltons (kDa) in an oral dosage form.

2. The composition according to claim 1, wherein the pro-inflammatory low molecular weight sodium hyaluronate fragments have a molecular weight of between 0.5 and 100 kDa.

3. The composition according to claim 1, wherein the algae based oil comprises Eicosapentaenoic (EPA) and Docosahexaenoic (DHA) fatty acids in the form of glycolipids and phospholipids.

4. The composition according to claim 1, wherein the algae based oil comprises 5 to 10 percent phospholipids and 35 to 40 percent glycolipids.

5. The composition according to claim 1, wherein the algae based oil includes at least 15 percent EPA fatty acids.

6. The composition according to claim 5, wherein the EPA fatty acids are conjugated with phospholipid and glycolipid polar lipids.

7. The composition according to claim 1, wherein the algae based oil is derived from the microalgae *Nannochloropsis oculata* comprising Eicosapentaenoic (EPA) fatty acids in the form of glycolipids and phospholipids.

8. The composition according to claim 1, wherein the algae based oil is derived from the microalgae selected from the group consisting of *thalassiosira* sp., *tetraselmis* sp., *chaetoceros* sp., and *isochrysis* sp., and comprising Eicosapentaenoic (EPA) and Docosahexaenoic (DHA) fatty acids in the form of glycolipids and phospholipids.

9. The composition according to claim 1, wherein the algae based oil is derived from the microalgae selected from the group consisting of *grateloupia turuturu; porphyridium cruentum; monodus subterraneus; phaeodactylum tricornutum; isochrysis galbana; navicula* sp.; *pythium irregule; nannochloropsis* sp.; and *nitzschia* sp. And comprising Eicosapentaenoic (EPA) and Docosahexaenioic (DHA) fatty acids in the form of *glycolipids* and *phospholipids*.

10. The composition according to claim 1, wherein the algae based oil is derived from the microalgae selected from the group consisting of *Asterionella japonica, Bidulphia sinensis, Chaetoceros septentrionale, Lauderia borealis, Navicula biskanteri, Navicula laevis (heterotrof.), Navicula laevis, Navicula incerta, Stauroneis amphioxys, Navicula pellicuolsa, Bidulphia aurtia, Nitzschia alba, Nitzschia chosterium, Phaeodactylum tricornutum, Phaeodactylum tricornutum, Skeletonema costatum, Pseudopedinella* sp., *Cricosphaera elongate, Monodus subterraneus, Nannochloropsis, Rodela violacea* 115.79, *Porphyry. Cruentum* 1380.2.Id, *Pavlova salina, Cochlodinium heteroloblatum, Cryptecodinium cohnii, Gonyaulax catenella, Gyrodinium cohnii, Prorocentrurn minimum, Chlorella minutissima, Isochrysis galbana* ALII4, *Phaeodactylum tricornutum* WT, *Porphyridium cruentum*, and *Monodus subterraneus* and comprising Eicosapentaenoic (EPA) and Docosahexaenoic (DHA) fatty acids in the form of glycolipids and phospholipids.

11. The composition according to claim 1, wherein the algae based oil is derived from a fungi selected from the group consisting of *Mortierella alpine, Mortierella alpine* IS-4, and *Pythium irregulare*, or a bacteria as SCRC-2738 and comprising Eicosapentaenoic (EPA) and Docosahexaenoic (DHA) fatty acids in the form of glycolipids and phospholipids.

12. The composition according to claim 1, wherein the astaxanthin is derived from *Haematococcus pluvialis*algae, *Pfaffia*, krill, or by synthetic routes, in the free dial, monoester or diester form.

* * * * *

UNITED STATES PATENT AND TRADEMARK OFFICE
CERTIFICATE OF CORRECTION

PATENT NO. : 9,238,043 B2
APPLICATION NO. : 14/217515
DATED : January 19, 2016
INVENTOR(S) : Minatelli et al.

It is certified that error appears in the above-identified patent and that said Letters Patent is hereby corrected as shown below:

Claims

Column 24, line 1:            Delete:
(Claim 10)                    "*Prorocentrurn*"

Insert:
                              -- *Prorocentrum* --

Column 24, line 16:           Delete:
(Claim 12)                    "dial"

Insert:
                              -- diol --

Signed and Sealed this
Twelfth Day of April, 2016

Michelle K. Lee
*Director of the United States Patent and Trademark Office*